United States Patent [19]

Rosenstatter

[11] Patent Number: 5,281,138
[45] Date of Patent: Jan. 25, 1994

[54] DENTAL HANDPIECE HAVING COAXIAL RING GEARS ROTATABLE AT DIFFERENT RESPECTIVE ANGULAR SPEEDS

[75] Inventor: Otto Rosenstatter, Seeham, Austria

[73] Assignee: Imtec Innovative Medizintechnik Gesellschaft m.b.H., Hallein, Austria

[21] Appl. No.: 928,743

[22] Filed: Aug. 13, 1992

[30] Foreign Application Priority Data

Aug. 13, 1991 [AT] Austria .................. 1592/91

[51] Int. Cl.⁵ ............................... A61C 1/02
[52] U.S. Cl. .................................... 433/105
[58] Field of Search ......................... 433/105

[56] References Cited

U.S. PATENT DOCUMENTS

| | | |
|---|---|---|
| 3,229,369 | 1/1966 | Hoffmeister et al. ............ 433/105 |
| 3,942,392 | 3/1976 | Page, Jr. et al. .................. 415/503 |
| 4,121,342 | 10/1978 | Flatland ............................. 433/105 |
| 4,433,957 | 2/1984 | Nakanishi ......................... 433/105 |

FOREIGN PATENT DOCUMENTS

| | | |
|---|---|---|
| 0012872 | 12/1982 | European Pat. Off. . |
| 0012871 | 5/1983 | European Pat. Off. . |
| 2717013 | 10/1978 | Fed. Rep. of Germany . |
| 2803933 | 10/1988 | Fed. Rep. of Germany . |

*Primary Examiner*—John J. Wilson
*Attorney, Agent, or Firm*—Wenderoth, Lind & Ponack

[57] ABSTRACT

A dental handpiece includes a drive shaft which is driven by a drive motor and which has two coaxial ring gears which can selectively be coupled to shafts passing through different tool carriers. Different angular speeds of the coaxial ring gears is achieved by the inner ring gear being directly connected to the drive shaft, whereas the outer ring gear is driven by the drive shaft by way of a planetary transmission.

6 Claims, 4 Drawing Sheets

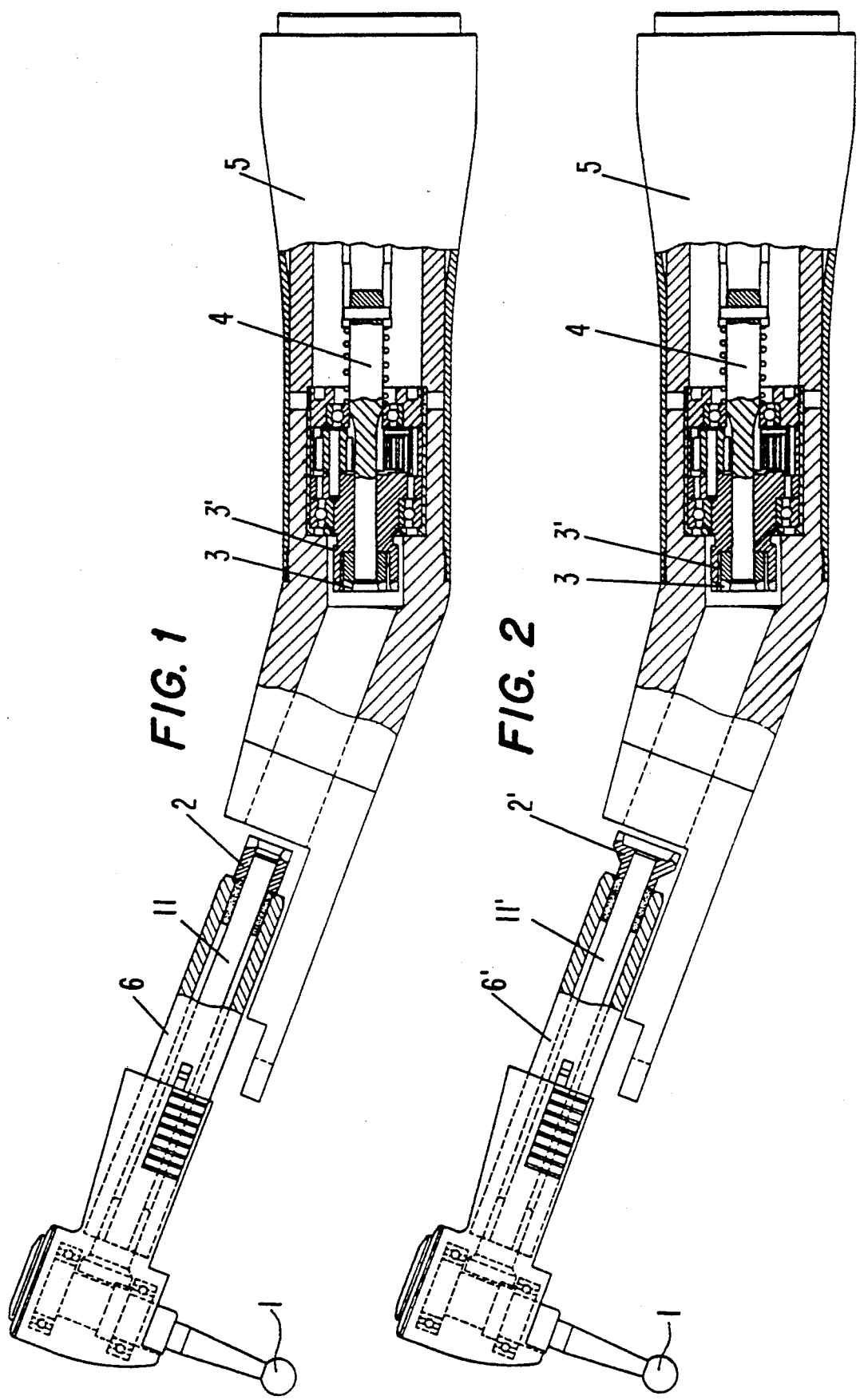

FIG. 3
FIG. 4
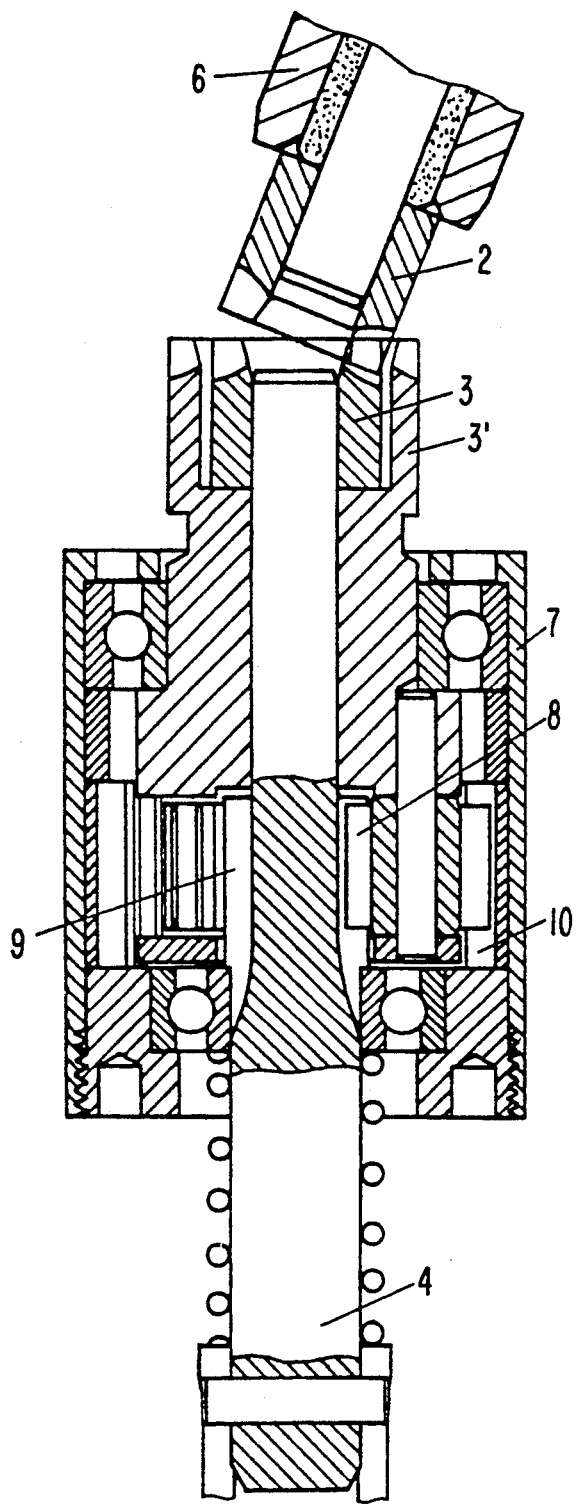
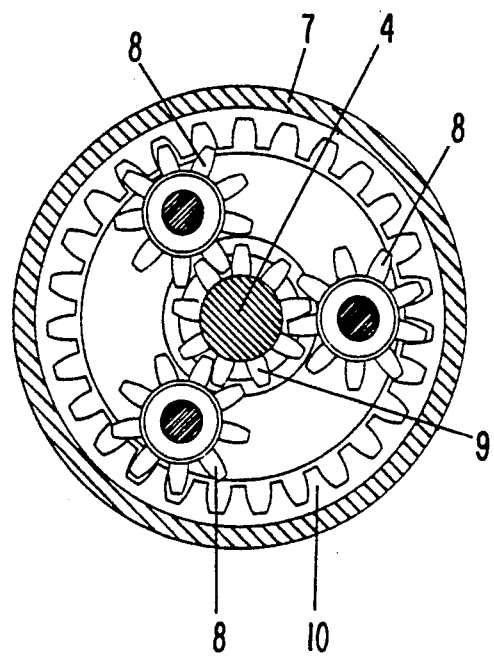

DENTAL HANDPIECE HAVING COAXIAL RING GEARS ROTATABLE AT DIFFERENT RESPECTIVE ANGULAR SPEEDS

BACKGROUND OF THE INVENTION

The invention relates to a dental handpiece comprising a drive shaft which is driven by a drive motor and which has two coaxial ring gears which can be selectively coupled to shafts passing through different tool carriers.

Handpieces of such type afford the advantage that tool carriers for tools involving a different speed of rotation only have to be connected to the appropriate ring gear in order to arrive at different drive transmission ratios for the tools.

In that respect, it is provided in EP-B1-0 012 871 that two coaxial ring gears are disposed on a common shaft and thus rotate at the same angular speed. In such arrangement the desired step-up or step-down transmission ratio is acheived by the tool carriers engaging by way of a small spur gear with the outer ring gear of the drive shaft or by way of a large spur gear engaging with the inner ring gear of the drive shaft. In that arrangement it is necessary for the shaft leading to the tool to be fitted to the drive shaft in an inclined and eccentric relationship, which on the one hand restricts the design options with regard to the shape of the handpiece while on the other hand requires the tool carrier to be of a relatively large diameter.

On the other hand, a construction of the type outlined in the opening part of this specification is known from EP-B1-0 012 872 (FIG. 10), in which a shaft can be arranged centrally in the tool carrier and various output drive speeds are achieved by using output drive shafts of different lengths. In that arrangement a gear at the end of the output drive shaft of the tool carrier that is towards the coupling means has a predetermined number of teeth, so that transmission ratios can only differ in accordance with differing numbers of teeth on the ring gears of the drive shaft. Another disadvantage with such construction is that the two transmission ratios require different directions of rotation.

It is already known, for example from U.S. Pat. No. 4,121,342, for different tool carriers to be driven selectively directly by way of a drive shaft or by way of a planetary transmission which is disposed around the drive shaft. The arrangement of a multi-stage planetary transmission (see DE-C-27 17 013) has also already been proposed, in order to be able to drive the output drive shaft of different tool carriers at different transmission ratios. A disadvantage of those handpieces which are necessarily straight in the region of the coupling means is the necessity of also having to effect manipulation in the handpiece for the purpose of changing the transmission ratio, in addition to exchanging the tool carrier.

SUMMARY OF THE INVENTION

In that respect, the general type of device as outlined in the opening part of this specification affords advantages, the underlying object of the present invention is that of eliminating the disadvantages which hitherto are still linked to such system. Therefore, the invention seeks to provide a device in which the transmission ratios can differ widely with the same direction of rotation, in which respect in particular a step-down transmission ratio is also to be possible. The invention seeks to provide that there is no limitation, by virtue of the nature of the coupling means, in terms of the design configuration of the handpiece, namely straight or angled. The invention further seeks to provide that the shafts in different tool carriers can have the same association with or relation to the handpiece.

In accordance with the invention, such objects are attained in that the angular speeds of the coaxial ring gears differ from each other.

Similarly to U.S. Pat. No. 4,121,342, with regard to the way in which the concept of the invention is carried into effect in structural terms, it can advantageously be provided that the different angular speeds of the coaxial ring gears is achieved by the inner ring gear being connected directly to the drive shaft, whereas the outer ring gear is driven by the drive shaft by way of a planetary transmission.

BRIEF DESCRIPTION OF THE DRAWINGS

Further details of the invention are described hereinafter with reference to the accompanying drawings, wherein:

FIGS. 1 and 2 are partly sectional views of different tool carriers which are coupled to the same handpiece in different ways;

FIG. 3 shows the coupling region of FIG. 1 on an enlarged scale and in the coupled condition;

FIG. 4 is a view in cross-section through the planetary transmission of FIG. 3;

DETAILED DESCRIPTION OF THE INVENTION

Figure 5:
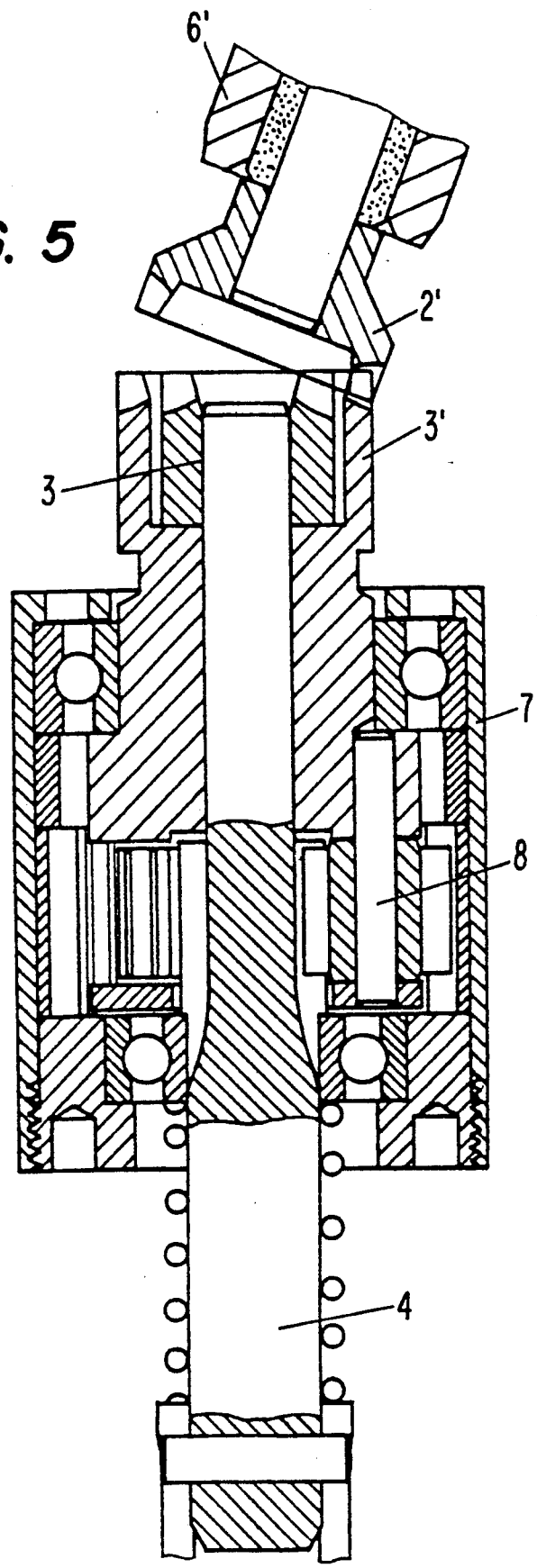
FIG. 5 is a view similar to FIG. 3 but showing the tool carrier of FIG. 2 in the coupled condition.

FIG. 1 shows a tool carrier 6 which a coaxial driving shaft 11 with can be coupled by a spur gear 2 to an inner ring gear 3 which is driven directly by a drive shaft 4 in a handpiece 5, by way of a motor (not shown). In FIG. 2 a shaft 11' of a tool carrier 6' can be coupled by way of a spur gear 2' to an outer ring gear 3' in the handpiece 5, which rotates at a lower speed than the ring gear 3. Such step-down effect with respect to the speed of the drive shaft 4 is produced by way of a planetary transmission 7 shown in FIGS. 3 and 4.

The planetary transmission 7 comprises in the usual fashion a sun gear 9 which is carried on the drive shaft 4 and which drives planet gears 8 which run on a fixed internally toothed member 10. The ring gear 3', with the planet gears 8 mounted thereto, rotates about the drive shaft 4, while the inner ring gear 3 is directly connected to the drive shaft 4.

In the case of the tool carrier 6 (FIG. 1 and FIG. 3), the arrangement illustrated provides for direct step-up transmission of the drive to the shaft 11 of the tool carrier, whereas in the case of the tool carrier 6' (FIG. 2 and FIG. 5), the planetary transmission 7 provides a step-down effect. If the ring gears 3, 3' have the same number of teeth as the associated spur gears 2, 2', it is possible in the same manner for the handpiece to be angled in the coupling region, as is shown in the drawings, or for the drive shaft to be extended rectilinearly by output drive shafts 11, 11'. In any event, in order to change the step-up or step-down transmission ratio, all that is necessary is to insert the respective tool carrier 6, 6' into one and the same handpiece 5, without further manipulative operations having to be carried out on the handpiece 5.

Figure 6:
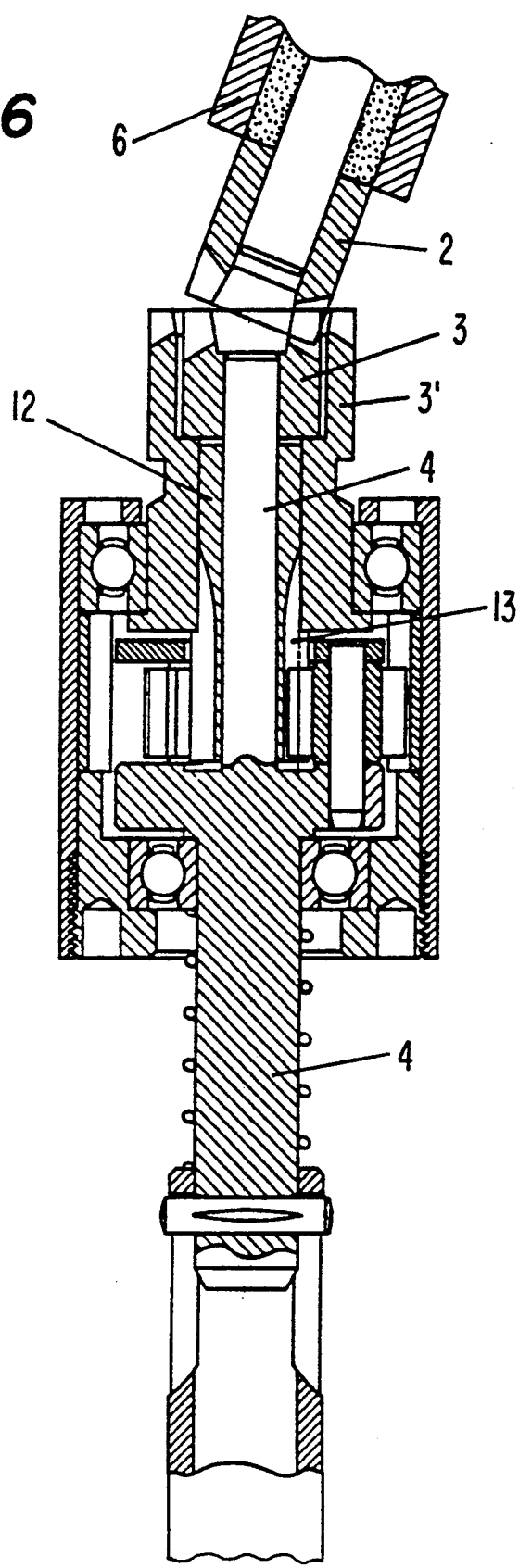
FIG. 6 is a view similar to FIG. 3 but showing a modified embodiment in which a step-up transmission ratio is provided by the planetary transmission.

In the embodiment shown in FIG. 6, the planetary transmission serves for stepping up the speed of the drive shaft 4. While therefore the ring gear 3 is carried directly on the drive shaft 4 and rotates therewith, the movement of the ring gear 3' to which the spur gear 2' of another tool carrier 6' can be selectively coupled takes place at a substantially higher speed. That is achieved by the axes of the planet gears 8 rotating with the drive shaft 4 and driving a sleeve 12 which is carried rotatably on the drive shaft 4. A front end of sleeve 12 is fixedly connected to the ring gear 3', while a rear end thereof has a tooth configuration 13 into which a tooth configuration of the planet gears 8 engage, similarly to Figure 4.

I claim:

1. In a dental handpiece including a drive shaft mounted for rotation about an axis thereof, a pair of coaxial ring gears mounted to be rotated in response to rotation of said drive shaft and forming separate output drive members of said dental handpiece, and a plurality of different tool carriers to be selectively coupled to said ring gears, the improvement comprising:

said pair of coaxial ring gears being mounted by means for rotating said ring gears at respective angular speeds that are different from each other.

2. The improvement claimed in claim 1, wherein a first said ring gear is directly connected to said drive shaft and is directly rotated thereby, and a second said ring gear is rotated by said drive shaft by means of a planetary transmission mounted therebetween.

3. The improvement claimed in claim 2, wherein said first ring gear is an inner ring gear, and said second ring gear is an outer ring gear positioned radially outwardly of said inner ring gear.

4. The improvement claimed in claim 3, wherein said planetary transmission comprises a sun gear rotatable with said drive shaft, a plurality of planetary gears meshing with said sun gear and rotatable thereabout, and said planetary gears being fixed to said outer ring gear, whereby said outer ring gear is rotatable relative to said inner ring gear.

5. The improvement claimed in claim 3, wherein said planetary transmission comprises a plurality of planetary gears fixed to said drive shaft for rotation therewith, a sleeve fixed to said outer ring gear and mounted to rotate relative to said drive shaft, and said planetary gears meshing with and rotating said sleeve, whereby said outer ring gear is rotatable relative to said inner ring gear.

6. The improvement claimed in claim 1, wherein said drive shaft comprises a single integral member having a drive output end that is fixedly positioned axially at a drive output end of said dental handpiece, and said pair of ring gears are fixedly positioned axially relative to said single integral member at said drive output end thereof.

* * * * *